US012582665B2

(12) United States Patent
Davis

(10) Patent No.: US 12,582,665 B2
(45) Date of Patent: Mar. 24, 2026

(54) TOPICAL COMPOSITION

(71) Applicant: FUTURA MEDICAL DEVELOPMENTS LIMITED, Guildford (GB)

(72) Inventor: Adrian Davis, Guildford (GB)

( * ) Notice: Subject to any disclaimer, the term of this patent is extended or adjusted under 35 U.S.C. 154(b) by 484 days.

(21) Appl. No.: 18/041,911

(22) PCT Filed: Apr. 12, 2021

(86) PCT No.: PCT/GB2021/050885
§ 371 (c)(1),
(2) Date: Feb. 16, 2023

(87) PCT Pub. No.: WO2022/038332
PCT Pub. Date: Feb. 24, 2022

(65) Prior Publication Data
US 2023/0330113 A1 Oct. 19, 2023

(30) Foreign Application Priority Data
Aug. 17, 2020 (GB) ...................................... 2012836

(51) Int. Cl.
| *A61K 31/00* | (2006.01) |
| *A61K 9/00* | (2006.01) |
| *A61K 9/06* | (2006.01) |
| *A61K 47/10* | (2017.01) |
| *A61K 47/12* | (2006.01) |

(52) U.S. Cl.
CPC .......... *A61K 31/658* (2023.05); *A61K 9/0014* (2013.01); *A61K 9/06* (2013.01); *A61K 47/10* (2013.01); *A61K 47/12* (2013.01)

(58) Field of Classification Search
CPC .................................................. A61K 31/658
See application file for complete search history.

(56) References Cited

U.S. PATENT DOCUMENTS

| 6,503,532 B1 | 1/2003 | Murty et al. |
| 2010/0273895 A1 | 10/2010 | Stinchcomb et al. |
| 2011/0052694 A1 | 3/2011 | Stinchcomb et al. |
| 2015/0182455 A1* | 7/2015 | Llamas ................. C12C 11/003 |
| | | 435/161 |
| 2016/0338974 A1 | 11/2016 | Aung-Din |
| 2021/0052511 A1* | 2/2021 | Callahan .............. A61K 9/0014 |

FOREIGN PATENT DOCUMENTS

| WO | 2010/126501 A1 | 11/2010 |
| WO | 2016/139471 A1 | 9/2016 |
| WO | 2017/173269 A1 | 10/2017 |
| WO | 2021/255483 A1 | 12/2021 |

OTHER PUBLICATIONS

European Patent Office, International Search Report issued in corresponding Application No. PCT/GB2021/050885, mailed Jul. 1, 2021.

United Kingdom Intellectual Property Office, Search Report issued in corresponding Application No. GB 2012836.9, dated Sep. 30, 2020.

* cited by examiner

*Primary Examiner* — Rei Tsang Shiao
(74) *Attorney, Agent, or Firm* — Stites & Harbison, PLLC; Terry L. Wright

(57) ABSTRACT

There is disclosed a composition for topical application of a cannabinoid as active ingredient comprising a solution of the cannabinoid in an excipient formulation comprising a polyhydric alcohol as partition coefficient enhancer, a saturated long-chain fatty acid or alcohol thereof as diffusion coefficient enhancer, and a co-solvent, wherein the saturated long-chain fatty acid or alcohol has a carbon chain length of from C10 to C16. The composition can be used in the treatment of a variety of conditions.

23 Claims, 2 Drawing Sheets

TOPICAL COMPOSITION

FIELD OF THE INVENTION

This invention relates to topical compositions comprising a cannabinoid, such as cannabidiol, as the active ingredient.

BACKGROUND TO THE INVENTION

Cannabinoids are believed to be effective in the treatment of a wide range of conditions including those involving pain, inflammation, and nausea, and specific disorders including epilepsy, anxiety disorders and glaucoma. A counter-indication to the widespread clinical use of cannabinoids, however, is their psychoactive properties. Nevertheless, one particular cannabinoid, cannabidiol (CBD), is recognised as being clinically effective without exhibiting such psychoactive effects.

The use of cannabinoids in the treatment of pain arising from a variety of disorders is considered to be of particular importance but, for oral application, a particular problem is that they are highly lipophilic, whereby their limited water solubility limits the amount available for absorption in the gastrointestinal tract. The efficacy of orally administered compositions is further compromised if the patient suffers from nausea or emesis since not only is the amount of active available for absorption diminished but patient compliance is discouraged. It is therefore desirable to have available a non-oral delivery route; especially where the target tissue is the skin or underlying tissues. Convenient possibilities for non-oral delivery are local, regional and transdermal delivery. Nevertheless, the lipophilic (and, thus, hydrophobic) nature of CBD (log P ~+6.00) militates against its inherent ability to be absorbed through the skin.

WO2010/127033 discloses pharmaceutical compositions suitable for, among other delivery options, topical application to the skin or other externally accessible membranes such as in the nose, ear, rectum or vagina. Topical application has the potential benefit of delivery of the active locally to the target site (where pain, for example, is being experienced) without causing an unnecessarily high concentration in the systemic circulation generally. The compositions disclosed by WO2010/127033, suitable for transdermal or topical delivery, comprise a cannabidiol (0.1-20% by weight) and excipients comprising a lower alcohol (15-95% by weight), a penetration enhancer (0.1-20% by weight) and water (balance to 100% by weight). The function of the penetration enhancer, which can be selected from a wide range of organic acids, esters, alcohols, ethers, sulphoxides, pyrollidones and terpenes, is to promote delivery of the active through the stratum corneum. A preferred penetration enhancer is diethylene glycol monoethyl ether.

Preferably, compositions disclosed in WO2010/127033 include a second penetration enhancer, desirably (where the first penetration enhancer comprised diethylene glycol monoethyl ether) isopropyl myristate. Further excipients may include a thickening agent, one or more antioxidants and propylene glycol. Compositions disclosed in WO2010/127033 may form a hydroalcoholic gel and may be used for topical treatment of arthritis and various skin disorders and conditions, joint pain, musculoskeletal pain and others. In preparation, the compositions may include a neutralising agent to adjust the viscosity to form a gel.

It is known to use so-called "co-enhancer" technology to improve transport of active compounds through the stratum corneum. Such technology has been described, for example, in WO2008/110741 and in WO2016/182159. In WO2008/

110741, a topical composition containing an NSAID as the active ingredient, especially diclofenac, is disclosed as comprising, for the excipient composition, a polyhydric alcohol, a glycol ether and an ester of a higher fatty acid. The function of the polyhydric alcohol, preferably a glycol such as propylene glycol, is to render the NSAID soluble in the stratum corneum and also to increase the solubility of the ester. The ester, preferably a polar lipid, increases the diffusivity through the stratum corneum. The glycol ether is a co-solvent to solubilise the polyhydric alcohol and the ester to form a homogeneous, single-phase carrier system for the NSAID. Thus, the polyhydric alcohol acts as a partition coefficient enhancer, the ester acts as a diffusion coefficient enhancer and the glycol ether acts as a co-solvent. Skin penetration of the active is primarily dependent on the dose of the partition coefficient enhancer, the degree of saturation of the active in the carrier composition and the degree of saturation of the diffusion coefficient enhancer in the carrier composition.

Optionally, the compositions described in WO2008/110741 include a volatile solvent such as a lower alcohol which also acts as a co-solvent for the other ingredients and solubilises the NSAID at saturation levels. On application to the skin, the volatile solvent evaporates thus driving the NSAID to supersaturation in the residual (non-volatile) phase are resulting in enhanced flux of the NSAID. As described in WO2008/110741, both the degree of saturation of the NSAID and the degree of saturation of the diffusion coefficient enhancer are important in use in determination of the flux of NSAID in skin penetration.

WO2016/132159 discloses that compositions described in WO2008/110741 can include water. Although, in use and on application to the skin, some water will evaporate with other volatile components, there will also be some water retained in the residual phase as an equilibrium mixture with the polyhydric alcohol, thus enhancing skin penetration flux and also inhibiting esterification of the NSAID by reaction with the polyhydric alcohol. It may also act as a non-solvent to reduce the solubility of the NSAID and, thus, to enhance the activity state as the volatile components evaporate.

One problem in designing an effective excipient vehicle for a cannabinoid, especially cannabidiol, seeking to take advantage of co-enhancer technology to increase skin penetration, is the extremely high solubility in organic media, for example exceeding 10% w/w in propylene glycol. Thus it is difficult to achieve a near-saturated solution except by using unacceptably high concentrations of the CBD. Furthermore, CBD or another cannabinoid when formulated in an excipient solution has a tendency towards instability, especially under oxidative stress and where the pH values lie outside the range approximately of pH 3 to 7. It is therefore not possible to provide an acceptable excipient formulation for a cannabinoid as active ingredient based on co-enhancer formulations such as disclosed in WO2008/110741 and WO2016/132159 as suitable for an NSAID such as diclofenac.

SUMMARY OF THE INVENTION

In order to provide a solution to the problems with known co-enhancer compositions as set out above, it has been found that the diffusion coefficient enhancer should comprise a long-chain fatty acid or alcohol thereof having a carbon chain length as from C10 to C16.

According to one aspect of the present invention, a composition for topical application of a cannabinoid as active ingredient comprises a solution of the cannabinoid in an excipient formulation comprising a polyhydric alcohol as partition coefficient enhancer, a saturated long-chain fatty acid or alcohol thereof as diffusion coefficient enhancer, and a co-solvent, wherein the saturated long-chain fatty acid or alcohol has a carbon chain length of from C10 to C16.

The saturated long-chain fatty acid or alcohol has a carbon chain length of from C10 to C16. Examples of such fatty acids include capric acid (decanoic acid), undecylic acid (undecanoic acid), lauric acid (dodecanoic acid), tridecylic acid (tridecanoic acid), myristic acid (tetradecanoic acid), pentadecylic acid (pentadecanoic acid), and palmitic acid (hexadecanoic acid). Examples of such fatty alcohols include capric alcohol (decanol), undecyl alcohol (undecanol), lauryl alcohol (dodecanol), tridecyl alcohol (tridecanol), myristyl alcohol (tetradecanol), pentadecyl alcohol (pentadecanol), and palmityl alcohol (hexadecanol). Preferably, the carbon chain length of the long-chain fatty acid or alcohol is C12 to C14. Preferred examples include lauric acid (dodecanoic acid), myristic acid (tetradecanoic acid) or myristyl alcohol (tetradecanoic alcohol). Preferably, the carboxylic acid or alcohol group is substituted at the 1-carbon position. The preferred diffusion coefficient enhancer is selected from myristic acid and myristyl alcohol, and more preferably comprises myristyl alcohol.

The target range for the concentration in compositions according to the invention of the cannabinoid is from 1 to 5% by weight, preferably 1 to 3%, and more preferably 2 to 3%. It has been found that, where the cannabinoid comprises cannabidiol, the use as diffusion coefficient enhancer of a C10 to C16 saturated carboxylic acid or alcohol enables the cannabidiol when present at a concentration within the target range to form a solution which is stable following (at least) four weeks' storage at 25° C.

The term "cannabinoid" means a biologically active terpenophenolic compound derived from the cannabis plant (*Cannabis sativa* or *Cannabis indica*) and/or molecule capable of interacting with classical cannabinoid receptors (CB1 and/or CB2). The cannabinoid may be any cannabinoid which is suitable for local, regional or transdermal delivery in a topical formulation. The cannabinoid may be naturally occurring within the cannabis plant, a decarboxylated derivative of a naturally occurring cannabinoid or a synthetic cannabinoid. Synthetic cannabinoids include biosynthetic cannabinoids that are produced using microorganisms which have been genetically engineered to contain the enzymatic pathway from cannabis plants that produces cannabinoids (for example, see Luo X et al., Complete biosynthesis of cannabinoids and their unnatural analogues in yeast, Nature. 2019; 567:123-126). Suitable cannabinoids include those with solubility characteristics similar to cannabidiol. For example, suitable cannabinoids include: cannabidiol; non-acidic, naturally occurring and synthetic derivatives such as cannabidorcol, nor-cannabidiol (CBD-C4), cannabidivarin and cannabidiol monomethyl ether; and other cannabis plant secondary metabolites derived from cannabigerolic acid and their decarboxylated products such as $\Delta^9$-tetrahydrocannabinol, cannabinol, cannabigerol, cannabichromene, cannabicyclol, cannabivarin, $\Delta^9$-tetrahydrocannabivarin, cannabichromevarin, cannabigerovarin, cannabigerol monomethyl ether, cannabielsoin and cannabicitran. Preferably, the cannabinoid is cannabidiol.

The co-solvent in compositions according to the invention may comprise a lower alcohol and/or a glycol ether. By "lower alcohol" is meant a C2 to C5 primary or secondary alcohol, for example ethanol or isopropyl alcohol. Although ethanol is more powerful than isopropyl alcohol as a co-solvent, it has been found to be more detrimental in terms of stability. As between ethanol and isopropyl alcohol in compositions according to the invention, therefore, isopropyl alcohol is preferred.

The glycol ether, if present, is preferably a diethylene glycol ether, for example diethylene glycol monoethyl ether (Transcutol). However, although Transcutol is a common ingredient in topical formulations generally, it appears in tests not to be effective in compositions according to the invention in that although it acts in promotion of epidermal penetration, it is detrimental in respect of transport through the skin into the receiving medium. It appears also to have a detrimental effect on stability. Overall, therefore, compositions according to the invention preferably do not include a glycol ether as a co-solvent.

Compositions according to the invention preferably include water. Water is a non-solvent for the cannabinoid and thus enable the solution of the cannabinoid in the excipients to be closer to saturation at the target range at from 1 to 5% by weight. In the absence of water, the saturated solubility of cannabidiol would be in excess of ten percent by weight.

In compositions according to the invention, the polyhydric alcohol used as the partition coefficient enhancer preferably comprises one or more glycols. The glycol may be selected from those having from 3 to 6 carbon atoms including propylene glycol, dipropylene glycol, 1,5-propanediol, butylene glycol and hexylene glycol, among others. Preferably, the polyhydric alcohol comprises propylene glycol, optionally together with butylene glycol.

The polyhydric alcohol in compositions according to the invention preferably has a concentration of from 25-50% by weight, more preferably 30-50% by weight, even more preferably 30-45% by weight, and most preferably 30-40% by weight. The long-chain fatty acid or alcohol preferably has a concentration of from 2-5% by weight, more preferably 2.5-4.5% by weight. In some embodiments, the long-chain fatty acid or alcohol has a concentration of from 2-3% by weight. The co-solvent is preferably 20-60% by weight, more preferably 20-50% by weight, and even more preferably 30-50% by weight. In some embodiments, the co-solvent is 30-40% by weight. If the composition includes water, it would be as a partial substitute for the co-solvent (e.g. lower alcohol) and preferably in a proportion up to 50% by weight of combined water and co-solvent or preferably from 35-50% of combined water and co-solvent, the combined water and co-solvents themselves comprising preferably from 50-65% of weight of the total composition. When considering the water in isolation of the co-solvent (e.g. lower alcohol), the water can have a concentration in the composition of from 20-30% by weight.

Optionally, glycerol, sorbitol or another polyhydric alcohol having three or more hydroxy groups may be included in compositions according to the invention together with the partition coefficient enhancer as a non-solvent for the cannabinoid and, thus, to enhance its activity state. The concentration of the polyhydric alcohol having three or more hydroxy groups, if present, would be up to about 15% of the total formulation, preferably up to 12.5%, for example 10% or up to 7.5%, for example 5%. Preferably, it should have a ratio of between 45:55 and 55:45 with the partition coefficient enhancer, preferably propylene glycol, to act as a non-solvent for the cannabinoid whilst not compromising stability.

Preferably compositions according to the invention have the physical form of a gel and are in a single phase, that is, they are stable and will not separate into distinct phases or form a precipitate on storage. Although silicone fluids are widely used in topical formulations, in the gel formulations of the current invention, and especially at higher water contents, they lead to phase separation. Thus silicone fluids and their derivatives, such as dimethicone silicon fluid, are preferably not used in compositions of the current invention. To promote a stable single phase, compositions may include an antinucleating polymer such as hydroxypropyl cellulose, hydroxypropylmethyl cellulose or other suitable cellulose; polyvinylpyrollidone or other suitable pyrollidone or a suitable acrylate/methacrylate. The preferred antinucleating agent comprises hydroxypropyl cellulose. Compositions may also include an anti-oxidant, for example a lipophilic antioxidant such as dibutylhydroxytoluene (BHT) or butylatedhydroxyanisole (BHA) or other antioxidant, for example sodium metabisulphite. Also optionally included are sensory signals such as menthol and/or eucalyptus oil or an agent which provides a skin-warming sensation, thickening or gelling agents, propellants for spray formulations and/or fragrance-enhancing agents.

Solvent systems for compositions according to the invention may comprise, in percentages by weight:

| cannabinoid | 1-5 |
| polyhydric alcohol | 20-50 |
| fatty acid/alcohol | 2-5 |
| co-solvent | 20-50 |
| water | 0-30 |

Preferably, such compositions comprise, in percentages by weight:

| cannabinoid | 2-3 |
| polyhydric alcohol | 30-45 |
| fatty acid/alcohol | 2.5-4.5 |
| co-solvent | 25-40 |
| water | 0-25 |

In some embodiments, compositions of the invention comprise, in percentages by weight:

| cannabinoid | 1-5 |
| polyhydric alcohol | 30-50 |
| fatty acid/alcohol | 2-5 |
| co-solvent | 20-40 |
| water | 20-30 |

In particular embodiments, compositions of the invention comprise, in percentages by weight:

| cannabinoid | 1-3 |
| polyhydric alcohol | 30-40 |
| fatty acid/alcohol | 2-3 |
| co-solvent | 30-40 |
| water | 20-30 |

In the embodiments above describing four particular compositions and the ranges of the components, a skilled person will appreciate that the paragraph above on page 6 which also describes preferred ranges for the various components is applicable to these four particular compositions such that one or more of the preferred ranges in the paragraph on page 6 can be substituted into the particular compositions.

Optional further ingredients such as thickening or gelling agents, antinucleating agents, sensory signals, fragrance-enhancing agents and propellants are generally present at concentrations respectively of 0.5-2.5% by weight.

The pH of the composition is preferably in the range 3-7, more preferably in the range 3-6, and even more preferably in the range 4-5.

According to a further aspect, the invention provides a topical composition for application of a cannabinoid for use in therapy.

The topical composition can be used in the treatment of a variety of conditions which are alleviated by a cannabinoid such as CBD. Such conditions include pain; inflammation; skin conditions such as dry skin, itchy skin, rashes, acne, eczema, dermatitis and psoriasis; damaged skin such as cuts, bruises, abrasions, blisters and wounds; baldness; alopecia; hair loss; and muscle spasms. The composition can be used by application to a target site on the human or animal body.

Further aspects of the invention include a method of treatment of the human or animal body by application to a target site of a topical composition containing a cannabinoid as active ingredient; and a method for the preparation of a medicament for the topical treatment of the human or animal body, all as hereinbefore described.

BRIEF DESCRIPTION OF THE DRAWINGS

The invention will now be described in detail by way of example only with reference to the figures in which.

EXAMPLES

Figure 1:
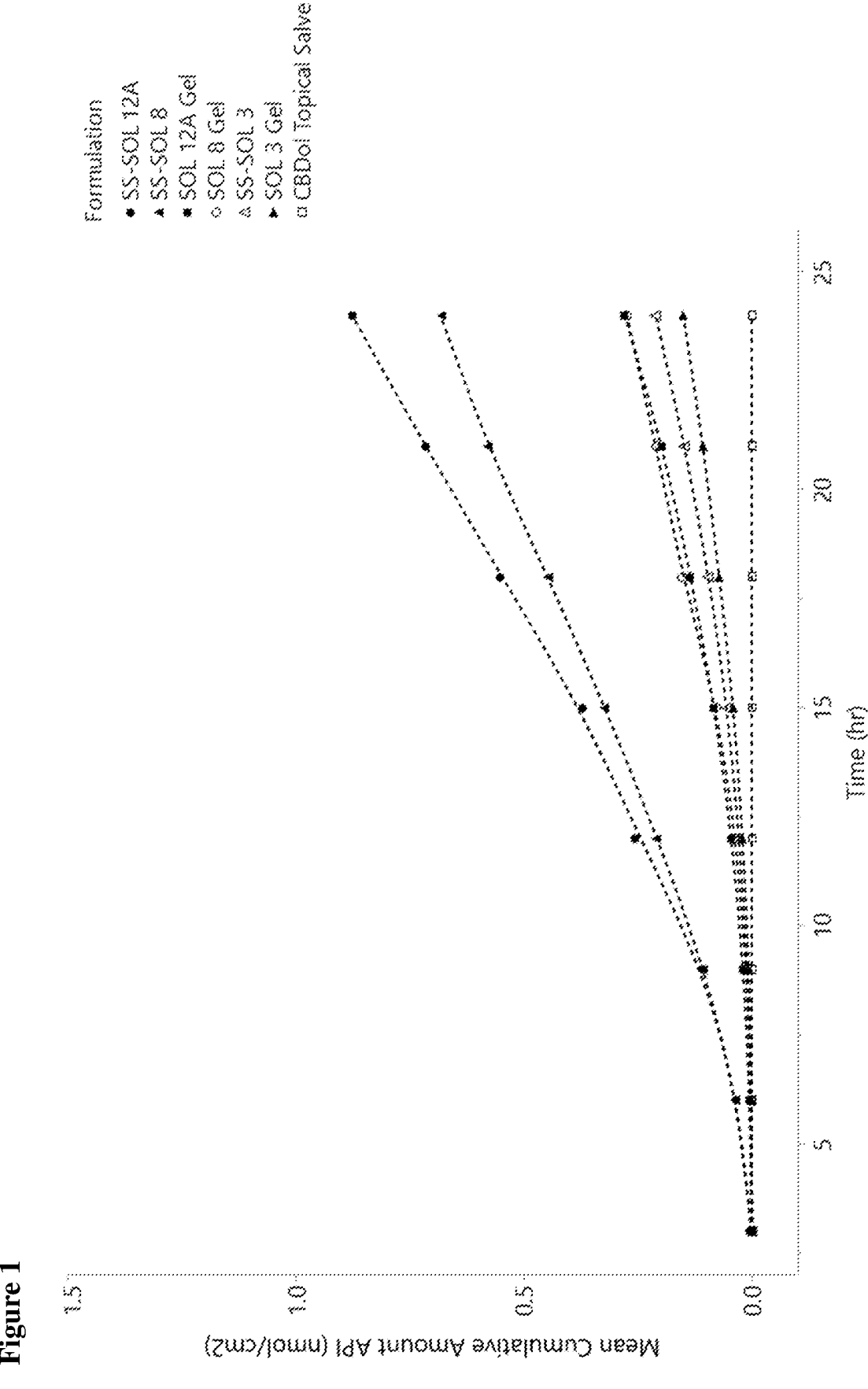
FIG. 1 is a graph showing the results of in vitro permeation and penetration (IVPT) studies for the compositions of the invention compared to an existing commercially available CBD formulation. The graph shows the mean cumulative amount of CBD (nmol/cm$^2$) delivered to the receptor solution 24 h post-application of the 7 formulations. Data points represent the cumulative amount of CBD from 3-5 replicates and 1 donor. Formulations listed in rank order. Outliers removed.

Exemplary solvent systems for compositions according to the invention are set out in the table below, together with a comparative formulation (SOL 1) based on the disclosure of WO2016/132159. The values given are percentages by weight.

TABLE 1

| | SOL 1 | SOL 3 | SOL 5 | SOL 12 |
|---|---|---|---|---|
| CBD | 2.0 | 2.0 | 2.0 | 2.0 |
| Propylene glycol | 30.56 | 42.31 | 35.00 | 35.00 |
| Transcutol | 14.09 | — | — | — |
| Isopropyl alcohol | 46.59 | 26.75 | 35.75 | 35.75 |
| Water | 5.00 | 24.75 | 24.75 | 24.75 |
| Isopropyl myristate | 1.76 | — | — | — |

TABLE 1-continued

|  | SOL 1 | SOL 3 | SOL 5 | SOL 12 |
|---|---|---|---|---|
| Lauric Acid | — | 4.19 | — | — |
| Myristic Acid | — | — | — | 2.50 |
| Myristyl Alcohol | — | — | 2.50 | — |
| By Weight | 100% | 100% | 100% | 100% |

The pH of all the formulations above was in the range 4-5.

Solvent systems such as those disclosed in the above table may be converted to gel formulations according to the invention by addition of one or more antioxidants and antinucleating agents.

Compositions as set out above may be prepared by mixing the various ingredients, in a manner known to those skilled in then art.

The Table below sets out exemplary solvent systems and corresponding gel formulations for compositions according to the invention:

TABLE 2

| Excipient | Composition (% w/w) | | | | | |
|---|---|---|---|---|---|---|
| | Gels | | | Solvent systems | | |
| | SOL12A | SOL8 | SOL3 | SS SOL12A | SS SOL8 | SS SOL3 |
| Cannabidiol (CBD) | 2.00 | 2.00 | 2.00 | 2.00 | 2.00 | 2.00 |
| Propylene glycol | 35.00 | 35.00 | 42.31 | 35.00 | 35.00 | 42.31 |
| Isopropyl alcohol (IPA) | 22.55 | 22.55 | 13.55 | 25.55 | 25.55 | 16.55 |
| Water | 24.75 | 24.75 | 24.75 | 24.75 | 24.75 | 24.75 |
| Myristyl alcohol | — | 2.50 | — | — | 2.50 | — |
| Myristic acid | 2.50 | — | — | 2.50 | — | — |
| Lauric acid | — | — | 4.19 | — | — | 4.19 |
| Butylated hydroxyanisole (BHA) | 0.10 | 0.10 | 0.10 | 0.10 | 0.10 | 0.10 |
| Butylated hydroxytoluene (BHT) | 0.10 | 0.10 | 0.10 | 0.10 | 0.10 | 0.10 |
| Hydroxy propylcellulose (HPC MF) | 3.00 | 3.00 | 3.00 | | N/A | |
| Total | 90.00 | 90.00 | 90.00 | 90.00 | 90.00 | 90.00 |
| pH adjustment solution | | | | to pH 4-5 | | |
| Final | | | | Q.S. to 100% with IPA | | |
| | 100.00 | 100.00 | 100.00 | 100.00 | 100.00 | 100.00 |

The SS SOL8 and SOL8 gel formulations above are based on the SOL 5 formulation from Table 1.

Skin Permeation and Penetration

The above compositions from Table 2 were tested for skin penetration efficacy against commercially-available CBDol Topical CBD Salve (manufactured by CBDistillery™) according to the following conditions:

TABLE 3

| SETUP | FULL SCALE IVPT |
|---|---|
| Skin type: | Epidermal Membrane |
| No. skin donors | 1 |
| Receptor solution: | PBS, pH 7.4 + 0.01% Brij 98 + 30 mM glutathione + 30 mM EDTA |
| No. formulations: | 7 |
| No. replicates: | 5 |
| No. skin blanks: | 1 |
| Dose amount: | 10 mg/cm² |
| Flow rate: | 8 µl/min |
| RS collection times: | Every 3 hours for 24 hours |
| SKIN PENETRATION SAMPLE PROCESSING* | |
| Extraction fluid: | 90:10 v/v acetonitrile:water + 0.1% BHT |
| Surface of skin: | Residual formulation was cleaned from the surface of the skin with 3 cotton swabs, one |

TABLE 3-continued

| SETUP | FULL SCALE IVPT |
|---|---|
| | dry, one wetted with extraction fluid and an additional dry one. Cotton swabs used to clean the skin were then discarded. |
| Stratum corneum: | No tape stripping was conducted, epidermis + stratum corneum was analyzed together. |
| Extraction procedure (SC & Epidermis): | No separation prior to processing. Epidermis and stratum corneum was homogenized in extraction fluid and shaken for 0.5-1 hour. |

Epidermal membrane was prepared by heat separating epidermis and dermis from dermatomed frozen human abdominal skin (from elective abdominoplasty), with the epidermal membrane being prepared on top of filter paper. The epidermal membrane from a single skin donor was mounted onto the MedFlux-HT® flow through diffusion cell system using a receptor solution of PBS pH 7.4 with 0.01% Brij 98, 30 mM glutathione and 30 mM EDTA, employing a flow rate of 8 µL/min. The formulation was applied as a single dose to the skin surface at 10 mg/cm² and receptor solution samples were collected every 3 hours over a 24 hour period.

Following completion of the experiment, the tissue was removed from the MedFlux-HT® flow through diffusion cell system. The surface of the tissue was cleaned with three cotton swabs (one dry, one wetted with 90:10 v/v acetonitrile:water with 0.1% BHT, and an additional dry cotton swab). Cotton swabs used to clean the surface of the skin were discarded. The tissue sample was then homogenised with 90:10 v/v acetonitrile:water with 0.1% BHT and shaken for approximately 0.5-1 hour. CBD amounts in the receptor solution and tissue were quantified by LC-MS/MS analysis.

Figure 2:
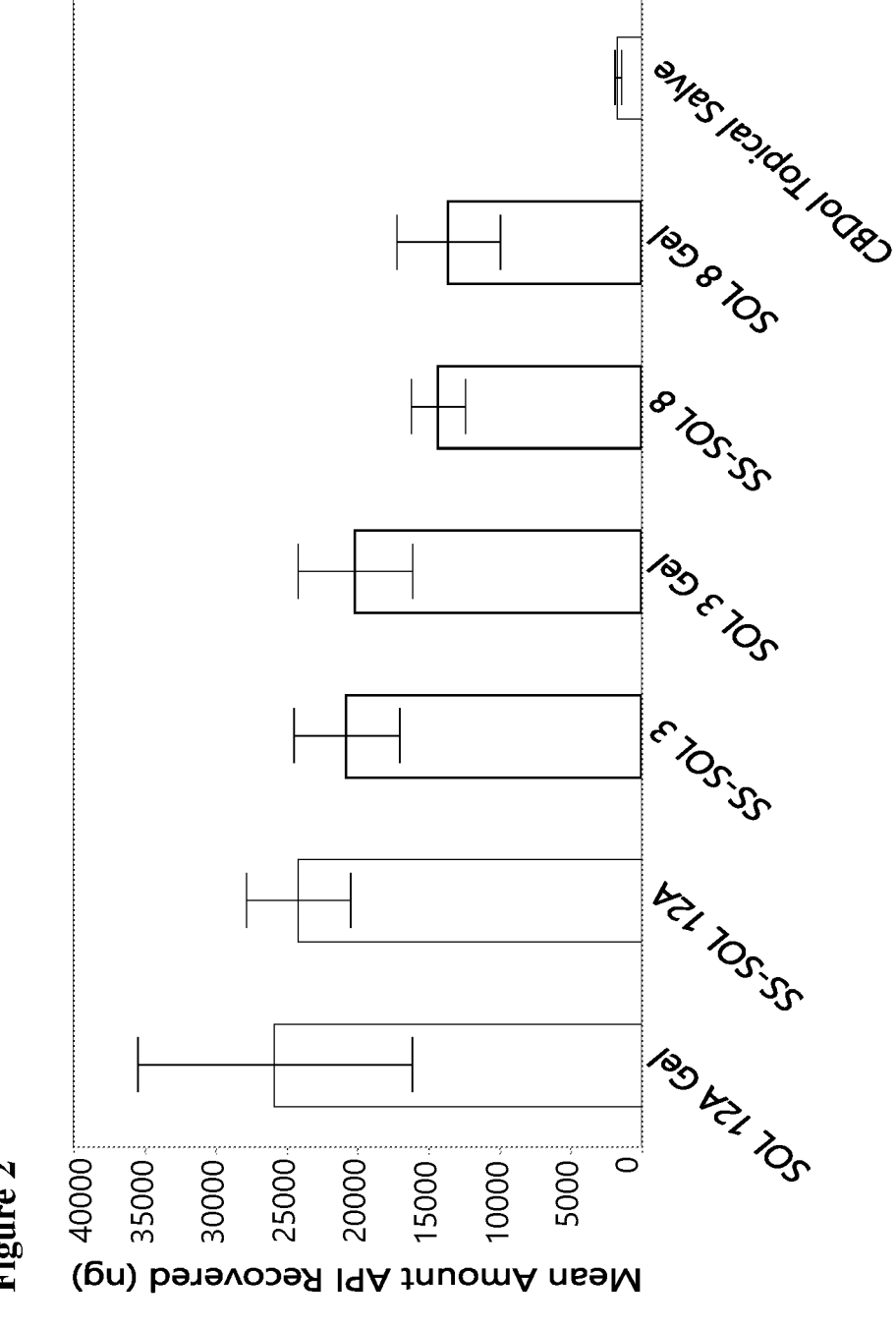
FIG. 2 is a graph showing the results of in vitro permeation and penetration (IVPT) studies for the compositions of the invention compared to an existing commercially available CBD formulation. The graph shows the mean amount of CBD (ng) delivered to the epidermis 24 h post-application of the 7 formulations. Data points represent the cumulative amount of CBD from 4-5 replicates and 1 donor. Error bars represent one standard error from the mean. Outliers removed.

The results are shown in Tables 4 and 5 below and graphically in FIGS. 1 and 2.

Receptor Solution—Tabulated Data (AUC and API Flux)

Mean cumulative amount of CBD (nmol/cm²) and API flux (nmol/cm²/hr) delivered to the receptor solution at 24 h, following application of the 7 formulations. Outliers removed.

TABLE 4

| Formulation | Cumulative Amt (nmol/cm$^2$) | | | | API Flux (nmol/cm$^2$/hr) | | | |
|---|---|---|---|---|---|---|---|---|
| | N | Mean | Std Dev | Std Err | N | Mean | Std Dev | Std Err |
| SS-SOL 12A | 3 | 0.88 | 0.72 | 0.42 | 3 | 0.053 | 0.029 | 0.017 |
| SS-SOL 8 | 5 | 0.68 | 0.57 | 0.25 | 5 | 0.034 | 0.018 | 0.008 |
| SOL 12A Gel | 5 | 0.28 | 0.13 | 0.06 | 5 | 0.028 | 0.013 | 0.006 |
| SOL 8 Gel | 5 | 0.27 | 0.21 | 0.09 | 5 | 0.022 | 0.016 | 0.007 |
| SS-SOL 3 | 4 | 0.21 | 0.07 | 0.03 | 4 | 0.021 | 0.007 | 0.004 |
| SOL 3 Gel | 5 | 0.15 | 0.02 | 0.01 | 5 | 0.015 | 0.003 | 0.001 |
| CBDol Topical Salve | 4 | 0.00 | 0.00 | 0.00 | 4 | 0.000 | 0.000 | 0.000 |

Epidermis Tabulated Data (ng)

Mean amount of CBD (ng) delivered to the epidermis at 24 h, following application of the 7 formulations. Outliers removed.

TABLE 5

| Formulation | Epidermis (ng) | | | |
|---|---|---|---|---|
| | N | Mean | Std Dev | Std Err |
| SOL 12A Gel | 5 | 25850 | 21576 | 9649 |
| SS-SOL 12A | 5 | 24200 | 8197 | 3666 |
| SS-SOL 3 | 5 | 20800 | 8338 | 3729 |
| SOL 3 Gel | 4 | 20200 | 8078 | 4039 |
| SS-SOL 8 | 5 | 14354 | 4265 | 1908 |
| SOL 8 Gel | 5 | 13630 | 8160 | 3649 |
| CBDol Topical Salve | 5 | 1698 | 537 | 240 |

It was found that all compositions tested outperformed the commercially-available product and delivered between about 14,000 and 26,000 ng of CBD to the skin, an 8-15-fold increase over CBDol Topical Salve. Compositions according to the invention delivered between 0.15-0.88 nmol/cm$^2$ to the receptor solution, whereas receptor solution samples for the comparator product were below the limit of quantification (lower limit of quantification=0.25 ng/mL). SS SOL12A and SS SOL8 delivered the highest amount of CBD to the receptor solution over 24 hours.

Stability

A known issue for CBD or other cannabinoid formulations is that there is a tendency towards instability, especially under oxidative stress and where the pH values lie outside the range approximately of pH 3 to 7. Further, certain excipients can cause cannabinoids to degrade. Therefore, over time, the CBD or other cannabinoid breaks down, affecting the shelf life of the composition. It has been shown that the compositions of the invention provide improved cannabinoid stability compared to commercially available formulations such as CBDol Topical CBD Salve. This means that the compositions maintain their potency over the course of their shelf life. Of the exemplary compositions described above, in stability testing, both SS SOL8 and SS SOL12A show no significant reduction in potency following storage at 25° C. and 40° C. for up to three months. SS SOL8 performed better than SS SOL12A in terms of recovery of and peak purity of CBD.

Data for the recovery of and peak purity of CBD for the SOL3, SOL8 and SOL12A formulations at after 1, 2, and 3 months is given in Tables 6 and 7 below.

TABLE 6

CBD percentage recovery (%) of the SOL3, SOL8 and SOL12A formulations at t = 0, 1, 2 and 3-month.

| | | | Percentage recovery (%) of CBD | | | | | |
|---|---|---|---|---|---|---|---|---|
| | | | t = 1 month | | t = 2 month | | t = 3 month | |
| Formulation | Pack | t = 0 | 25° C./ 60% RH | 40° C./ 75% RH | 25° C./ 60% RH | 40° C./ 75% RH | 25° C./ 60% RH | 40° C./ 75% RH |
| SOL3 | Tube | 101.50 | 93.96 | 93.51 | 97.43 | 96.16 | 101.35 | 95.42 |
| 2% w/w CBD | Vial | | 98.16 | 96.77 | 99.58 | 94.99 | 98.62 | 96.01 |
| SOL8 | Tube | 98.97 | 100.29 | 98.90 | 99.94 | 99.80 | 102.87 | 102.30 |
| 2% w/w CBD | Vial | | 100.39 | 98.32 | 100.92 | 99.99 | 100.07 | 98.32 |
| SOL12A | Tube | 101.94 | 98.42 | 94.47 | 97.96 | 96.68 | 98.77 | 96.94 |
| 2% w/w CBD | Vial | | 98.34 | 97.01 | 97.80 | 94.47 | 98.39 | 95.24 |

TABLE 7

Peak purity (% area) of the SOL3, SOL8 and SOL12A formulations at t = 0, 1, 2 and 3-month.

| | | | Peak purity (% area) | | | | | |
|---|---|---|---|---|---|---|---|---|
| | | | t = 1 month | | t = 2 month | | t = 3 month | |
| Formulation | Pack | t = 0 | 25° C./ 60% RH | 40° C./ 75% RH | 25° C./ 60% RH | 40° C./ 75% RH | 25° C./ 60% RH | 40° C./ 75% RH |
| SOL3 | Tube | 99.35 | 98.51 | 96.04 | 98.15 | 94.27 | 97.64 | 91.99 |
| 2% w/w CBD | Vial | | 99.00 | 97.26 | 98.54 | 95.03 | 97.78 | 93.66 |
| SOL8 | Tube | 99.25 | 99.04 | 98.90 | 99.23 | 98.75 | 99.19 | 98.37 |
| 2% w/w CBD | Vial | | 99.25 | 98.96 | 99.24 | 97.87 | 98.63 | 96.58 |
| SOL12A | Tube | 99.23 | 98.55 | 96.10 | 98.38 | 94.77 | 97.88 | 92.43 |
| 2% w/w CBD | Vial | | 98.89 | 96.43 | 98.52 | 94.40 | 98.05 | 92.88 |

The invention claimed is:

1. A composition for topical application of a cannabinoid as active ingredient comprises a solution of the cannabinoid in an excipient formulation comprising a polyhydric alcohol as partition coefficient enhancer, a saturated long-chain fatty acid or alcohol thereof as diffusion coefficient enhancer, and a co-solvent, wherein the saturated long-chain fatty acid or alcohol has a carbon chain length of from C10 to C16, wherein the composition comprises, in percentages by weight:

| | |
|---|---|
| cannabinoid | 1-5 |
| polyhydric alcohol | 20-50 |
| fatty acid/alcohol | 2-5 |
| co-solvent | 20-50 |
| water | 0-30. |

2. The composition according to claim 1, wherein the long-chain fatty acid or alcohol has a carbon chain length of from C12 to C14.

3. The composition according to claim 1, wherein the long-chain fatty acid or alcohol is myristic acid or myristyl alcohol.

4. The composition according to claim 1, wherein the long-chain fatty acid or alcohol is myristyl alcohol.

5. The composition according to claim 1, wherein the co-solvent comprises a lower alcohol and/or a glycol ether.

6. The composition according to claim 5, wherein the lower alcohol is isopropyl alcohol.

7. The composition according to claim 5, wherein the glycol ether is a diethylene glycol ether.

8. The composition according to claim 1, wherein the co-solvent is a lower alcohol.

9. The composition according to claim 1, wherein the polyhydric alcohol is one or more glycols.

10. The composition according to claim 1, wherein the polyhydric alcohol is propylene glycol, optionally together with butylene glycol.

11. The composition according to claim 1, wherein the composition further comprises water.

12. The composition according to claim 1, wherein the composition further comprises glycerol, sorbitol or a second polyhydric alcohol having three or more hydroxy groups.

13. The composition according to claim 1, wherein the composition is in a single phase.

14. The composition according to claim 1, wherein the composition is in the form of a gel.

15. The composition according to claim 1, wherein the composition does not include a silicone fluid.

16. The composition according to claim 1, wherein the composition comprises, in percentages by weight:

| | |
|---|---|
| cannabinoid | 2-3 |
| polyhydric alcohol | 30-45 |
| fatty acid/alcohol | 2.5-4.5 |
| co-solvent | 25-40 |
| water | 0-25. |

17. The composition according to claim 1, wherein the composition comprises, in percentages by weight:

| | |
|---|---|
| cannabinoid | 1-3 |
| polyhydric alcohol | 30-40 |
| fatty acid/alcohol | 2-3 |
| co-solvent | 30-40 |
| water | 20-30. |

18. The composition according to claim 1, wherein the cannabinoid is selected from cannabidiol; non-acidic, naturally occurring and synthetic derivatives; and other cannabis plant secondary metabolites derived from cannabigerolic acid and their decarboxylated products.

19. The composition according to claim 1, wherein the cannabinoid is cannabidiol.

20. A method of treatment comprising applying an effective amount of the composition of claim 1 to a target site on a human or animal body, wherein the method is for the treatment of: pain; inflammation; skin conditions; damaged skin; baldness; alopecia; hair loss; and muscle spasms.

21. The method of claim 20, wherein the skin conditions are selected from dry skin, itchy skin, rashes, acne, eczema, dermatitis and psoriasis, and wherein the damaged skin is selected from cuts, bruises, abrasions, blisters and wounds.

22. The composition according to claim 1, wherein the co-solvent is isopropyl alcohol.

23. The composition according to claim 1, wherein the cannabinoid is selected from cannabidiol, cannabidorcol, nor-cannabidiol (CBD-C4), cannabidivarin, cannabidiol monomethyl ether, $\Delta^9$-tetrahydrocannabinol, cannabinol, cannabigerol, cannabichromene, cannabicyclol, cannabivarin, $\Delta^9$-tetrahydrocannabivarin, cannabichromevarin, cannabigerovarin, cannabigerol monomethyl ether, cannabielsoin and cannabicitran.

* * * * *